United States Patent [19]

Snader et al.

[11] 4,127,646

[45] Nov. 28, 1978

[54] SUBSTITUTED 2H-PYRAN-2,6(3H)-DIONE DERIVATIVES

[75] Inventors: Kenneth M. Snader, Hatboro, Pa.; Chester R. Willis, Wilmington, Del.

[73] Assignee: SmithKline Corporation, Philadelphia, Pa.

[21] Appl. No.: 812,550

[22] Filed: Jul. 5, 1977

Related U.S. Application Data

[63] Continuation-in-part of Ser. No. 696,461, Jun. 16, 1976, abandoned.

[51] Int. Cl.[2] ........................ A61L 9/04; A61K 31/35; C07D 309/22; C07D 309/30

[52] U.S. Cl. ........................................ 424/45; 424/283; 260/343.5; 260/345.7 R; 260/345.9 R

[58] Field of Search .................. 260/345.9 R, 345.7 R, 260/343.5; 424/283, 45

[56] References Cited

U.S. PATENT DOCUMENTS 4,032,652 6/1977 Chakrin et al. ............... 260/345.9 R

*Primary Examiner*—Nicky Chan
*Attorney, Agent, or Firm*—Richard D. Foggio

[57] ABSTRACT

Substituted 2H-pyran-2,6(3H)-dione derivatives useful in the treatment of allergic conditions are prepared by reaction of 3,5-diacetyl-4,6-dihydroxy-2H-pyran-2-one with an appropriate aniline.

17 Claims, No Drawings

SUBSTITUTED 2H-PYRAN-2,6(3H)-DIONE DERIVATIVES

This application is a continuation-in-part of application Ser. No. 696,461 filed June 16, 1976 now abandoned.

This invention relates to substituted 2H-pyran-2,6(3H)-dione derivatives which are useful for inhibiting the symptoms of an allergic response resulting from an antigen-antibody reaction. More specifically, the compounds of this invention are believed to be effective by inhibiting the release and/or formation and release of pharmacologically active mediators such as histamine, serotonin and slow-reacting substance of anaphylaxis (SRS-A) from effector cells which are produced and/or released as a result of an interaction of antigen and specific antibody fixed to the cell surface (allergic reaction). These properties enable the subject compounds to be useful in various allergic diseases such as asthma, rhinitis and urticaria.

The compounds of this invention are represented by the following general structural formula:

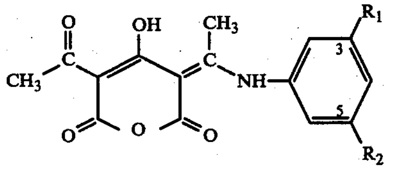

FORMULA I wherein:

$R_1$ and $R_2$ represent amino, alkanoylamino or methylsulfonamido; and the alkanoyl moieties have from 2 to 5 carbon atoms, straight or branched chain.

Particular compounds of this invention represented by formula I above are 3,5-bis-acetamido; 3,5-bis-propionamido; 3,5-bis-methylsulfonamido; 3,5-diamino and 3-amino-5-acetamido derivatives.

The compounds of formula I are conveniently prepared as shown in the following scheme:

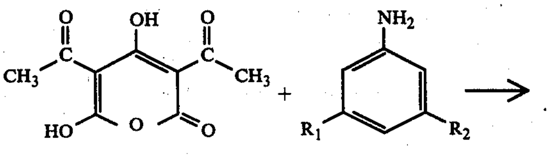

-continued

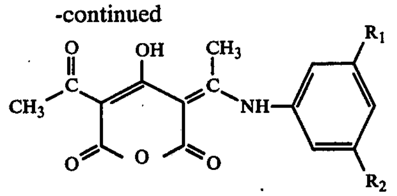

in which $R_1$ and $R_2$ are alkanoylamino or methylsulfonamido. Thus, 3,5-diacetyl-4,6dihydroxy-2H-pyran-2one and the appropriately substituted aniline are heated at reflux in an inert organic solvent such as benzene, toluene, ethanol or methanol for from one to three hours to give the products.

To prepare the compounds of formula I wherein one or both of $R_1$ and $R_2$ is amino, a substituted 5-nitroaniline or 3,5-dinitroaniline in reacted as above with the pyran-2-one to give the corresponding nitro substituted derivatives which are hydrogenated catalytically with palladium-on-carbon to obtain the free amino products.

Mono-and di-alkali metal salts of the compounds of formula I, such as the mono-and di-sodium or potassium salts are readily obtainable by treatment with the appropriate alkali metal alkoxide, for example methoxide, in an alkanol solvent such as methanol. Similarly, the free amino products ($R_1/R_2$ is amino) may be used in the form of a pharmaceutically acceptable acid addition salt, for example, those formed with either an inorganic or organic acid such as maleic, fumaric, methanesulfonic, acetic, hydrochloric, hydrobromic or sulfuric acids.

The pyran2-one starting material indicated above is obtained by reaction of acetonedicarboxylic acid with acetic anhydride in sulfuric acid at elevated temperature. The reaction product actually has the tautomeric structure as shown below:

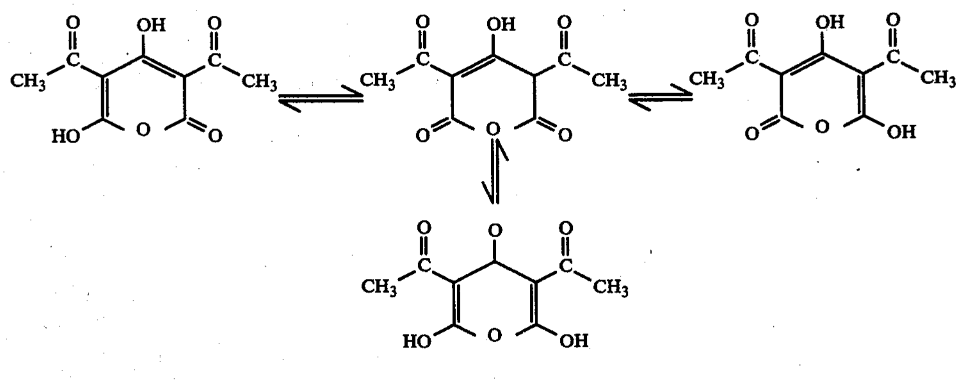

Ⓐ however for convenience it is designated herein as 3,5-diacetyl-4,6-dihydroxy-2H-pyran-2-one. Accordingly, the reaction of this product with an aniline as shown above gives a product having the tautomeric structures as shown below:

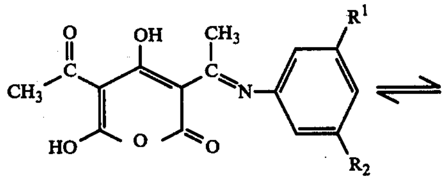

Ⓑ

-continued

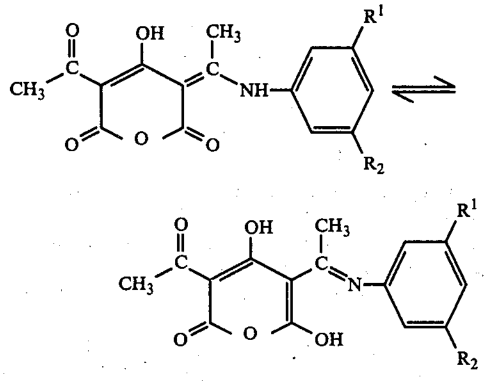

in which $R_1$ and $R_2$ are as defined above for formula I. For convenience we have chosen to use one tautomeric form, namely the intermediate enamine pyran-2,6-dione structure, to represent all of the compounds formed by reaction of Ⓐ with the aniline, as indicated by formula I above. It will be apparent however to one skilled in the art that the more complete representation of the compounds of formula I is shown by the tautomerization Ⓑ

The substituted aniline starting materials used herein are conveniently prepared by well-known preparative methods.

Wiley, R. H. et al. J. Org. Chem. 21:686-688 (1956) has reported the reaction of amines with the reaction product of acetonedicarboxylic acid and acetic anhydride, the latter designated 5-carboxydehydroacetic acid. Similarly, Kiang, A. K. et al. J. Chem. Soc. (c) pp. 2721-6 (1971) has disclosed such reaction products with amines. However there is no disclosure of products represented by formula I.

The inhibitory activity of the compounds of this invention on mediator release in sensitized tissues, thereby inhibiting the effects of the allergic reaction, is measured by the ability of the test compound to inhibit the passive cutaneous anaphylaxis (PCA) reaction in rats. In this test system, titered and appropriately diluted serum (from rats previously immunized by the intraperitoneal injection of ovalbuminaluminum hydroxide or ovalbumin-i.m.-Bordatella pertussis U.S.P. i.p.-and N-Brasiliensis i.p.) containing reaginic antibodies directed against ovalbumin is injected intradermally at four sites on the shaved backs of normal adult male rats. Forty-eight hours later the animals are injected intravenously with 0.5 ml. of isotonic saline solution containing 5 mg. of the ovalbumin antigen and 5 mg. of Evans blue dye. Chemical mediators such as histamine and serotonin which are released at the sensitized sites as a result of a local cellular anaphylaxis, cause an increase in capillary permeability with resultant leakage of plasma and formation of a wheal. The wheal is visualized by the plasma protein-bound Evans blue dye. Under conditions of the test, the average control wheal is approximately 12×12 mm. Thirty minutes following antigen challenge, the animals are killed, the dorsal skin is reflected and the diameter of the wheals recorded. A test compound is administered intravenously, initially at 0.5 minutes prior to antigen challenge (longer pretreatment times and other routes of drug administration, i.e. oral or intraperitoneal, may be employed). Percent inhibition is calculated from the difference in mean average wheal diameter between a treated group and saline or appropriate diluent controls.

The interruption by a test compound of the sequence of events triggered by reaginic antibody-antigen interaction on the surface of sensitized cells is indicative of utility in inhibiting the symptoms which result from an immediate-type allergic response.

The compounds of formula I administered intravenously to rats at doses of from 0.005 to 10 mg/kg produce marked inhibition of the PCA reaction. For example, 5-acetyl-3-[1-(3,5-bis-propionamidophenylamino)ethylidene]-4-hydroxy-2H-pyran-2,6(3H)-dione produced 62% inhibition of the rat PCA wheal at 0.005 mg/kg, i.v. Another compound, 5-acetyl-3-[1-(3,5-bis-methylsulfonamidophenylamino)ethylidene]-4-hydroxy-2H-pyran-2,6(3H)-dione, produced 50% inhibition of the rat PCA wheal at 0.25 mg/kg, i.v. and 5-acetyl-3-[1-(3-amino-5-acetamidophenylamino)ethylidene]-4-hydroxy-2H-pyran-2,6(3H)-dione produced 96% inhibition of the rat PCA wheal at 0.25 mg/kg, i.v.

In testing for mechanism of action the compounds of formula I, following i.v. administration at the same dose and pretreatment time which exhibited significant inhibition of the rat 48-hour PCA reaction, do not provide comparable inhibition of wheals of equal severity produced in rats by the intracutaneous administration of histamine and serotonin.

Upon oral administration, 5-acetyl-3-[1-(3,5-bis-propionamidophenylamino)ethylidene]-4-hydroxy-2H-pyran-2,6-(3H)-dione produced 32% inhibition in the rat 48-hour PCA system at 25 mg/kg and a pretreatment time of 15 minutes.

The compounds of this invention may be administered in conventional pharmaceutical compositions comprising an appropriate amount of a compound of formula I in association with a pharmaceutical carrier or diluent. The nature of the composition and the pharmaceutical carrier or diluent will of course depend upon the intended route of administration, i.e. orally, parenterally or by inhalation. Usually a compound is administered to an animal in a composition comprising an amount sufficient to produce an inhibition of the symptoms of an allergic response. When employed in this manner, the dosage of the composition is such that from 0.5 mg. to 500 mg. of active ingredient are administered at each administration. For convenience equal doses will be administered 1 to 4 times daily with the daily dosage regimen being about 0.5 mg. to about 2000 mg.

In general, particularly for the prophylactic treatment of asthma, the compositions will be in a form suitable for administration by inhalation. Thus the compositions will comprise a suspension or solution of the active ingredient in water for administration by means of a conventional nebulizer. Alternatively the compositions will comprise a suspension or solution of the active ingredient in a conventional liquified propellant such as dichlorodifluoromethane or chlorotrifluoroethane to be administered from a pressurized container. The compositions may also comprise the solid active ingredient diluted with a solid diluent, e.g. lactose, for administration from a powder inhalation device. In the above compositions, the amount of carrier or diluent will vary but preferably will be the major proportion of a suspension or solution of the active ingredient. When the diluent is a solid it may be present in less, equal or greater amounts than the solid active ingredient.

A wide variety of other pharmaceutical forms can be employed. Thus, if a solid carrier is used the preparation can be tableted, placed in a hard gelatin capsule in powder or pellet form, or in the form of a troche or lozenge for oral administration. The amount of solid carrier will vary widely but preferably will be about 25 mg. to about 1 g. If a liquid carrier is used, the preparation will be in the form of a syrup, emulsion, soft gelatin capsule, sterile injectable liquid such as an ampul, or an aqueous or non-aqueous liquid suspension.

Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly the carrier or diluent can include any time delay material well known to the art, such as glyceryl monostearate or glyceryl distearate alone or with a wax.

The pharmaceutical preparations thus described are made following the conventional techniques of the pharmaceutical chemist involving mixing, granulating and compressing when necessary, or variously mixing and dissolving the ingredients as appropriate to the desired end product.

Included within the scope of this invention is the method of inhibiting the symptoms of an allergic response resulting from an antigen-antibody reaction which comprises administering to an animal a therapeutically effective amount for producing said inhibition of a compound of formula I, preferably in the form of a pharmaceutical composition. The administration may be carried out in dosage units at suitable intervals or in single doses as needed. Usually the method of this invention will be practiced when relief of allergic symptoms is specifically required, however, the method is also usefully carried out as continuous or prophylactic treatment. A particular application is a method of relieving or preventing allergic airway obstruction which comprises administering to an animal a therapeutically effective amount at suitable intervals. It is within the skill of the art to determine by routine experimentation the effective dosage to be administered from the dose range set forth above, taking into consideration such factors as the degree of severity of the allergic condition being treated, and so forth.

The following examples illustrate the preparation of compounds of formula I and their incorporation into pharmaceutical compositions and as such are not to be considered as limiting the invention set forth in the claims appended hereto.

EXAMPLE 1

To a solution of 1.5 g. (0.01 mol) of 3,5-diaminonitrobenzene in 3 ml. of pyridine cooled to 5° C. was added 1.6 ml. (0.02 mol) of methanesulfonyl chloride, dropwise, and the mixture was stirred for 90 minutes at room temperature. The reaction mixture was decomposed by adding dilute hydrochloric acid and ice. The solid was filtered, washed with water and dried to give 3,5-bis-methylsulfonamidonitrobenzene, m.p. 223°-224° C.

A mixture of 1.5 g. (0.005 mol) of 3,5-bis-methylsulfonamidonitrobenzene in 100 ml. of ethanol and 300 mg. of 10% palladium-on-carbon was hydrogenated in a Parr apparatus until hydrogen uptake had ceased. The catalyst was filtered, the ethanol was removed under reduced pressure and the residue was dissolved in 30 ml. of methanol. This solution of 3,5-bis-methylsulfonamidoaniline (1.36 g.) and 1.06 g. (0.005 mol) of 3,5-diacetyl-4,6-dihydroxy-2H-pyran-2-one was refluxed for two hours under nitrogen. The reaction mixture was filtered to give 5-acetyl-4-hydroxy-3-[1-(3,5-bis-methylsulfonamidophenylamino)ethylidene]-2H-pyran-2,6(3H)-dione, m.p. 260° C.

EXAMPLE 2

A mixture of 25 g. (0.108 mol) of 3,5-dinitrobenzoyl chloride in 65 ml. of glacial acetic acid was stirred vigorously and 7.5 g. (0.108 mol) of sodium azide was added. After stirring for one hour at room temperature, the reaction mixture was poured into 300 ml. of cold water and chilled in an ice bath. The crude azide was filtered and air dried overnight.

The 3,5-dinitrobenzoyl azide thus obtained (5 g., 0.021 mol) was heated gently in 20 ml. of concentrated sulfuric acid until nitrogen evolution was complete. The resulting solution was poured over 200 ml. of ice/water and then made basic to pH 10 with concentrated aqueous ammonia solution. The solid was filtered to give 3,5-dinitroaniline.

To a mixture of 7.5 g. (0.038 mol) of 3,5-dinitroaniline and 75 ml. of ethanol was added 70 ml. of an ammonium sulfide solution (prepared by saturating a mixture of 100 g. of ethanol and 54 g. of concentrated aqueous ammonia with hydrogen sulfide). After refluxing for three hours, the reaction mixture was cooled, acidified to pH 1 with concentrated hydrochloric acid, filtered and concentrated in vacuo to about 100 ml. The solution was made basic to pH 10 with concentrated aqueous ammonia to precipitate 3,5-diaminonitrobenzene, m.p. 141°-142° C.

A mixture of 2.5 g. (0.015 mol) of 3,5-diaminonitrobenzene, 100 ml. of toluene, 15 ml. of acetic acid and 3 ml. (3.24 g., 0.32 mol) of acetic anhydride was refluxed for five hours. The reaction mixture was cooled, filtered and the solid washed well with toluene, then boiled in 150 ml. of ethanol for 20 minutes to give 3,5-bis-acetamidonitrobenzene, m.p.>290° C.

This nitrobenzene (1.3 g., 0.0052 mol) was hydrogenated in a mixture of 200 ml. of ethanol and 0.3 g. of 10% palladium-on-carbon in a Parr apparatus at room temperature. The aniline product was obtained upon usual workup.

To a refluxing mixture of 0.96 g. (0.0045 mol) of 3,5-diacetyl-4,6-dihydroxy-2H-pyran-2-one in 35 ml. of methanol was added a solution of 1 g. (0.0045 mol) of 3,5-bis-acetamidoaniline (prepared as above) in 15 ml. of methanol. After three hours at reflux, the reaction mixture was cooled and filtered to yield 5-acetyl-4-hydroxy-3-[1-(3,5-bis-acetamidophenylamino)ethylidene]-2H-pyran-2,6(3H)-dione, m.p. 265°-267° C. (dec.).

Both the mono-and di-sodium salts are prepared upon treatment of the dione with sodium methoxide in methanol.

EXAMPLE 3

To a mixture of 1.8 g. of 3,5-diaminonitrobenzene and 20 ml. of propionic acid was added 5 ml. of propionic anhydride and the resulting mixture was heated at reflux for 30 minutes. The cooled reaction mixture was poured over ice/water and stirred for one hour. Filtration gave the product 3,5-bis-propionamidonitrobenzene, m.p. 197°-198° C.

Following the procedures outlined in Example 2, this nitrobenzene was hydrogenated to the 3,5-bis-propionamidoaniline and the latter (2.15 g., 0.0084 mol) was reacted with 1.75 g. (0.0084 mol) of 3,5-diacetyl-4,6-dihydroxy-2H-pyran-2-one to furnish 5-acetyl-4-hydroxy-3-[1-(3,5-bis-propionamidophenylamino)e- thylidene]-2H-pyran-2,6(3H)-dione, m.p. 239°–241° (dec.).

Similarly, reaction of 3,5-diaminonitrobenzene in isobutyric acid with isobutyric anhydride furnishes the 3,5-bis-isobutyramidonitrobenzene which is further reacted as outlined in Example 2 to yield 5-acetyl-4-hydroxy-3-[1-(3,5-bis-isobutyramidophenylamino)ethylidene]-2H-pyran-2,6-(3H)-dione.

EXAMPLE 4

A mixture of 10 g. (0.0546 mol) of 3,5-dinitroaniline (prepared as in Example 2) and 25 ml. of glacial acetic acid was heated until all the solid dissolved. Acetic anhydride (10ml. ) was added and the resulting mixture was refluxed for 10 minutes. Cooling and diluting to 350 ml. with water gave 3,5-dinitroacetanilide, m.p. 190°–191° C.

The acetanilide thus prepared (9.5 g., 0.042 mol) was refluxed in a mixture of 140 ml. of ethanol and 140 ml. of ammonium sulfide solution (prepared as in Example 2). Evaporation of ethanol in vacuo, filtration and treatment of the filtrate with concentrated aqueous ammonia solution gave 3-acetamido-5-nitroaniline, m.p. 204°–205° C.

The nitroaniline (3.8 g., 0.0195 mol) was refluxed with 4.1 g. (0.0195 mol) of 3,5-diacetyl-4,6-dihydroxy-2H-pyran-2-one in 120 ml. of methanol for two hours. The reaction mixture was filtered hot, isolating 5-acetyl-4-hydroxy-3-[1-(3-acetamido-5-nitrophenylamino)ethylidene]-2H-pyran-2,6(3H)-dione, m.p.>270° C.

This dione (1 g., 0.00256 mol) was hydrogenated at room temperature in a mixture of 100 ml. of ethanol, 0.3 g. of 10% palladium-on-carbon and 0.3 ml. of concentrated hydrochloric acid on a Parr apparatus. The reaction mixture was filtered and the filter cake was stirred in 40 ml. of dimethylformamide under argon. Filtering again and treatment of the filtrate with 200 ml. of water yielded 5-acetyl-4-hydroxy-3-[1-(3-amino-5-acetamidophenylamino)ethylidene]-2H-pyran-2,6(3H)-dione, hydrate, m.p. 227°–230° C. (dec.).

Treatment of the product thus obtained, in tetrahydrofuran solution, with etheral hydrogen chloride gives the corresponding hydrochloride salt.

As a specific embodiment of a composition of this invention, an active ingredient such as 5-acetyl-4-hydroxy-3-[1-(3,5-bis-methylsulfonamidophenylamino)ethylidene]-2H-pyran-2,6(3H)-dione is dissolved in sterile water at a concentration of 0.5% and aerosolized from a nebulizer operating at an air flow adjusted to deliver the desired aerosolized weight of drug.

For oral administration, a composition such as the following can be prepared.

| Ingredients | Mg./Tablet |
|---|---|
| 5-Acetyl-4-hydroxy-3-[1-(3,5-bis-propionamido-phenylamido)ethylidene]-2H-pyran-2,6(3H)-dione | 10 |
| Calcium sulfate, dihydrate | 150 |
| Sucrose | 25 |
| Starch | 15 |
| Talc | 5 |
| Stearic acid | 3 |

The sucrose, calcium sulfate and active ingredient are thoroughly mixed and granulated with hot 10% gelatin solution. The wetted mass is passed through a #6 mesh screen directly onto drying trays. The granules are dried at 120° F. and passed through a #20 mesh screen, mixed with the starch, talc and stearic acid, and compressed into tablets.

EXAMPLE 5

Following the procedures of Example 4, an equimolar mixture of 3,5-dinitroaniline and 3,5-diacetyl-4,6-dihydroxy-2H-pyran-2-one in methanol was reacted to give 5-acetyl-4-hydroxy-3-[1-(3,5-dinitrophenylamino)ethylidene]-2H-pyran-2,6(3H)-dione. A solution of the latter (3.0 g., 0.008 mol) in 30 ml. of dimethylformamide was hydrogenated over 200 mg. of 10% palladium-on-carbon at 50 psi. When absorption stopped the catalyst was filtered and the filtrate poured into 200 ml. of ice-water. The resulting product was filtered, washed with water and dried to give 5-acetyl-4-hydroxy-3-[1-(3,5-diaminophenylamino)ethylidene]-2H-pyran-2,6(3H)-dione, m.p. above 350° C. (dec.).

Analysis, Calculated -C: 55:98 H: 4.86 N: 13.06. Found -C: 56.17 H: 5.17 N: 13.14.

This compound produced 68% inhibition of the rat PCA wheal at 0.625 mg/kg, i.v. and 61% inhibition in the rat 48-hour PCA system after oral administration of 0.20 mg/kg.

What is claimed is:

1. A compound represented by the formula:

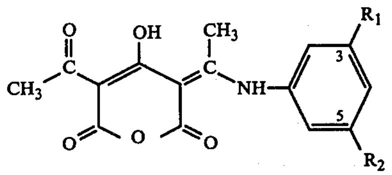

wherein:

$R_1$ and $R_2$ represent amino, alkanoylamino or methylsulfonamido; and the alkanoyl moieites have from 2 to 5 carbon atoms, straight or branched chain, or a mono-or di-alkali metal salt of said compound, or a pharmaceutically acceptable acid addition salt of said compound when $R_1$ or $R_2$ is amino.

2. A compound according to claim 1 in which $R_1$ and $R_2$ are alkanoylamino.

3. A compound according to claim 2 in which $R_1$ and $R_2$ are acetamido.

4. A compound according to claim 2 in which $R_1$ and $R_2$ are propionamido.

5. A compound according to claim 1 in which $R_1$ and $R_2$ are methylsulfonamido.

6. A compound according to claim 1 in which $R_1$ is amino and $R_2$ is acetamido.

7. A compound according to claim 1 in which $R_1$ and $R_2$ are amino.

8. A pharmaceutical composition for inhibiting the symptoms of asthma comprising a nontoxic pharmaceutical carrier or diluent and an amount sufficient to produce said inhibition of a compound represented by the formula:

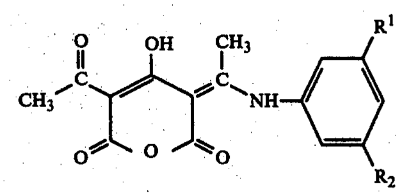

wherein:

$R_1$ and $R_2$ represent amino, alkanoylamino or methylsulfonamido; and the alkanoyl moieties have from 2 to 5 carbon atoms, straight or branched chain, or a mono-or di-alkali metal salt of said compound, or a pharmaceutically acceptable acid addition salt of said compound when $R_1$ or $R_2$ is amino.

9. A pharmaceutical composition according to claim 8 in a form suitable for administration by inhalation.

10. A pharmaceutical composition according to claim 8 comprising a solution or suspension of the active ingredient in sterile water.

11. A pharmaceutical composition according to claim 8 in the form of an aerosol formulation.

12. A pharmaceutical composition according to claim 8 in which the pharmaceutical carrier or diluent is a solid.

13. A pharmaceutical composition according to claim 8 in which $R_1$ and $R_3$ are propionamido.

14. A pharmaceutical composition according to claim 8 in which $R_1$ and $R_2$ are methylsulfonamido.

15. A pharmaceutical composition according to claim 8 in dosage unit form and in which the active ingredient is in an amount of from about 0.5 mg. to about 500 mg. per dosage unit.

16. A method of inhibiting the symptoms of asthma which comprises administering to an animal in need of said inhibition a therapeutically effective amount for producing said inhibition of a compound represented by the formula

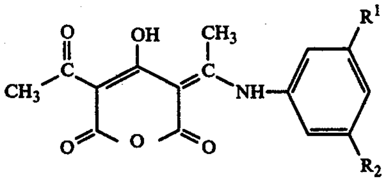

wherein:

$R_1$ and $R_2$ represent amino, alkanoylamino or methylsulfonamido; and the alkanoyl moieties have from 2 to 5 carbon atoms, straight or branched chain, or a mono-or di-alkali metal salt of said compound, or a pharmaceutically acceptable acid addition salt of said compound when $R_1$ or $R_2$ is amino.

17. The method according to claim 16 in which the active ingredient is administered in a daily dosage regimen of from about 0.5 mg. to about 200 mg.

* * * * *